(12) United States Patent
Prusik et al.

(10) Patent No.: US 6,544,925 B1
(45) Date of Patent: Apr. 8, 2003

(54) ACTIVATABLE TIME-TEMPERATURE INDICATOR SYSTEM

(75) Inventors: Thaddeus Prusik, Stroudsburg, PA (US); Raymond M. Arnold, Harrisonville, NJ (US); Allan P. Piechowski, Califon, NJ (US)

(73) Assignee: LifeLines Technology, Inc., Morris Plains, NJ (US)

( * ) Notice: Subject to any disclaimer, the term of this patent is extended or adjusted under 35 U.S.C. 154(b) by 0 days.

(21) Appl. No.: 09/517,831

(22) Filed: Mar. 2, 2000

(51) Int. Cl.$^7$ ................................................ B41M 5/30
(52) U.S. Cl. ........................................ 503/201; 503/226
(58) Field of Search .................................... 503/200, 226, 503/201; 428/913; 436/2, 7; 116/206, 207, 216, 218; 422/56–58; 252/408.1

(56) References Cited

U.S. PATENT DOCUMENTS

| | | | | |
|---|---|---|---|---|
| 4,057,029 A | * | 11/1977 | Seiter ..................... | 116/114 V |
| 5,053,339 A | * | 10/1991 | Petel ........................ | 436/2 |
| 5,085,802 A | * | 2/1992 | Jalinski .................... | 252/408.1 |
| 5,254,473 A | * | 10/1993 | Petel ........................ | 436/1 |

* cited by examiner

Primary Examiner—Bruce H. Hess
(74) Attorney, Agent, or Firm—Lionel N. White

(57) ABSTRACT

An activatable time-temperature indicator system useful in tracking the thermal exposure history of a temperature-sensitive perishable product and providing a visually-distinct signal, such as a change in color density, at the expiration of a predetermined time-temperature integral comprises a first element, such as a direct thermal printing label (11), comprising a composition (13) having at least a first co-reactant of a color-forming reaction. A second, activator element, such as an adhesive tab (21) capable of being affixed to the label element, comprises an activator component (25), such as a second co-reactant of the color-forming reaction or a solubilizing agent for prompting the interaction of the co-reactants of the label composition. The activator tab element is affixed to the label composition to activate for reaction at ambient conditions the normally high-temperature color-forming composition (13) of the label at about the same time as the label is affixed to the perishable product. Such an ability to effect the initiation of the indicator reaction at a given time eliminates any unknown, premature color formation in the indicator system to thereby ensure a true time-temperature history of the perishable product.

20 Claims, 3 Drawing Sheets

ACTIVATABLE TIME-TEMPERATURE INDICATOR SYSTEM

BACKGROUND OF THE INVENTION

The present invention relates to an indicator system which is responsive at a temperature-dependent rate to yield a visually-distinct indication of cumulative thermal exposure of an associated product in excess of a predetermined time-temperature integral. More particularly, the invention relates to such a system which is attached to a unit of thermally-sensitive perishable product and is activated at the time of introduction of the unit into commerce to initiate the monitoring of the unit's cumulative exposure to harmful temperatures. The system provides for the generation of a visually-distinct color which signals the end-point of the safe, useful shelflife of the product when the allowable time-temperature integral is exceeded. In a preferred embodiment, the indicator system of the invention comprises the use of a direct thermal label paper and an additional element which is applied to the label to react therewith and initiate a time- and temperature-dependent color change useful in monitoring the cumulative ambient temperature exposure of a labeled perishable product.

Color-forming or color-changing temperature-sensitive indicators which are capable of monitoring the handling of perishable goods are generally known and their use for this purpose is increasing. The utility of such indicators is to signal when a perishable article to which the indicator is attached has reached the point of quality loss, or unsafe condition, due to periods of excessive temperature exposures after which the product should no longer be used, or the product should be closely scrutinized to ensure suitable quality prior to being used. Indicator systems of this nature are important to ensure the quality and safety of perishable foods, pharmaceuticals, chemicals, and other such sensitive items.

In the case of perishable foods, modern packaging technologies are employed in an attempt to extend the shelf life of such products as meat, poultry, and fish. For example, plastic films with various gas permeabilities and barrier properties are used to maintain gas mixtures in the package to reduce the proliferation of aerobic spoilage organisms. However, the microbiology of food contained in this type of package permits anaerobic pathogens to grow in this modified gas atmosphere under suitable temperature conditions with no organoleptic sign of spoilage. A food product thus exposed to such temperature abuse can produce a lethal concentration of pathogens, yet provide no discernable sign of spoilage, a condition which can lead to serious health consequences if the product is consumed. It is therefore a safety feature for the consumer to have an indicator system associated with the perishable product in order to provide some visual indication that can warn of exposure of the product beyond an acceptable combination of time and temperature, i.e. a critical "time-temperature integral".

With respect to highly perishable foodstuffs, e.g., meat, poultry, and fish, it is advantageous for the indicator system to be placed on each unit of sale so that continuous monitoring is carried out from the time of packing until the time of use. Otherwise, there would be no indication that a packaged product has been subjected to an unknown temperature excursion, such as could result during transportation and distribution or from intermittent customer handling or removal from a refrigerated case, which could lead to significant quality degradation and health endangerment.

In order to be most effective, indicator systems should be formulated and employed to provide a visual indication, such as a change in color, contemporaneously with the generation of conditions of spoilage in the associated perishable products. To this end indicator systems should ideally have a rate of visual change paralleling the deterioration rate of the associated product. Although such an ideal performance is not readily achievable in view of the myriad conditions influencing product spoilage, indicator systems should at least be operable only during their association with a product. That is to say, an effective indicator system should not be susceptible of responding to or registering temperature gradients to which it has itself been exposed between the time of its own manufacture and the time it is ultimately attached to the intended perishable product. Only in this manner is an indicator system able to reliably monitor the complete thermal history of an associated perishable product throughout the various phases of that product's storage and distribution.

In earlier attempts to meet the need for independent response in time-temperature indicator systems, such as freeze/thaw monitors and shelflife markers, the indicator product, in the form of label, tag device, or the like, was isolated from actinic temperatures immediately upon manufacture, such as by freezing or at least cooling to a non-active temperature. For example, widely-used labels comprising diacetylene monomer inks registering irreversible color generation upon polymerization as a function of ambient temperature were required to be stored from the time of manufacture at temperatures below the threshold of significant color-forming polymerization. Such expedients were effective as long as storage and handling conditions were scrupulously monitored; however, these indicator system products were themselves subject to the same vagaries of human behavior as were the perishable products they were intended to protect, and the desired reliability could be compromised. The expenditure, albeit occasionally futile, of equipment and resources in an attempt to ensure the required storage conditions sometimes outweighed the initial cost of the indicator product.

Thus, apart from the fundamental requirements of reproducibility and economical production, an acceptable indicator system must be isolated in an economical and "fail-safe" manner from conditions which would otherwise initiate its own temperature response reaction and detract from its ability to register a true time-temperature integral vis-a-vis a given perishable product with which it is ultimately to be associated. The most reliable such means for isolation is to formulate or configure the indicator system to be in an inactive state which is made active only at the time of its association with the product unit to be monitored. The present invention provides such an economical, reliable, and activatable time-temperature indicator system.

A number of activatable time-temperature indicator systems have previously been proposed, yet none provides a ready and economical means for preventing premature initiation of the underlying temperature-sensitive indicator reaction. In a majority of such systems which comprise, for example, a label which is to be affixed to a perishable product, potential co-reactant components, such as precursors to an ambient temperature color-forming reaction, are located in close proximity, as in contiguous layers or interspersed mixtures, yet are maintained in reactive isolation by means of additional intervening layers, encapsulating films, or the like. Each of such isolating means, however, introduces additional expenses of resources and manufacturing operations. Further, these indicator products continue, due to the close proximity of potential reactants, to be susceptible to inadvertent, premature activation, such as where pressure-rupturable isolating encapsulations are subjected to mishandling or dormant light-sensitive co-reactants experience vagrant actinic exposure, or where other acceptable storage conditions are exceeded.

Another consideration which has contributed to the limited acceptability of currently-available activatable indicator systems is the excessive economic expenditures in materials and manufacturing operations resulting from the requirement for indicator and activating compositions or means to be individually formulated and assembled, along with isolation means, into the final composite indicator system product. Thus, from the viewpoint of economical acceptability alone, it is desirable to make available to the industry a time-temperature indicator product which comprises the use of a minimum of effective and low-cost components and resources.

To this end, the present invention utilizes as a visually-responsive co-reactant element a readily-available common or commodity material, such as a heat-printable label product which comprises a composition, e.g., a mixture of potentially-reactive color-forming precursors, having inherent resistance to activation under less than extraordinary ambient conditions of temperature or the like. The invention further comprises an additional, economical activator product element to be combined with the visually-responsive label product at the time of ultimate application to a perishable product to be monitored. In this manner the invention not only eliminates potential dangers of premature indicator activation, it also reduces significantly the expense of a dedicated time-temperature indicator system by incorporating as a major component existing, readily-available general-purpose, visually-responsive products, such as temperature-responsive thermographic commodity labels.

Thermally-responsive marking or printing products, particularly direct thermal label products, are currently in wide distribution and use. Due to their simple response to heated marking indicia, these clean, non-smearing products are instrumental in the rapid replacement of marking or printing equipment requiring replenishment of inks or colored printing ribbons. Thus, thermal printing devices are incorporated to a nearly universal degree in point-of-sale labeling equipment, such as weighing scales and other dispensing devices employed at locations marketing perishable foods and other commodities. It is in conjunction with thermographic label products used at such locations that the time-temperature indicator activator element product embodiments of the present invention find particular application.

SUMMARY OF THE INVENTION

The present invention comprises a time-temperature indicating system for monitoring the elapse of a combination of time and ambient temperature. Such a system is particularly useful in monitoring the exposure of a perishable foodstuff or commodity product to a critical integral of such time and temperature which would result in spoilage or unacceptable degradation of the quality of the perishable product.

In a preferred embodiment, the invention takes the form of a label having a paper or film substrate bearing a coating comprising a first, or primary, composition which is thermally-responsive to yield a visually-apparent change, such as development or intensification of a color. This embodiment further comprises a second composition, either self-formed or borne on a second substrate, which is combined in contact with the label coating to activate or facilitate an ambient thermal response of the primary composition. From the moment of such activation, typically effected at the moment of association of the label, by self-adhesion or other common means, with a unit of perishable product, the thermally-responsive composition of the combination system proceeds inexorably in its color-forming reaction, at a varying rate influenced by ambient temperature, toward the critical integral of time and temperature which, by a predetermined level of developed color density, will signal the end of useful life of the associated perishable product.

The primary composition label may preferably be a self-adhesive thermographic label commonly dispensed from weighing station equipment at supermarkets, delicatessens, fast-meal emporia, meat, fish, and poultry processing plants, and the like and which generally takes the form of a "direct thermal paper" comprising a primary color-forming high-temperature printing composition. Other products incorporating thermographic compositions, such as facsimile and thermal-imaging papers and films, represent additional sources of first composition element components useful in the present invention.

The second, activating element component preferably takes the form of a self-adhesive tab or label comprising a substrate and an adhesive composition which additionally comprises an activating component that, e.g., when applied to the direct thermal label coating, combines with the primary composition to enable its color-forming reaction, for example, to proceed within a lower temperature range than that required for the designed thermographic response of the label product, the lower range being typically that which lies above the range of safe storage temperatures for the subject perishable product and within which product spoilage or quality deterioration is likely to occur. In variant embodiments, the activating co-reactant component may be further prevented from premature action upon the primary color-forming composition by isolation within pressure-rupturable capsules or may comprise a photolabile compound requiring exposure to actinic radiation. Alternatively, the activating composition may be applied directly, e.g., in fluid or laminate form, to the primary composition coating at the time of point-of-sale label marking and application to the subject product unit.

In yet another embodiment of the invention, the activating tab composition may comprise as the activating component a co-reactant which when combined with one or more of the reactant components of the primary high-temperature printing composition will form a secondary color-forming composition which proceeds at its own temperature-dependant reaction rate within a lower intermediate ambient temperature range that presents the danger of food or perishable spoilage. Where the intermediate range of spoilage temperature may vary within an enterprise location, e.g., as differing among fish, meat, and poultry within a supermarket environment, a variety of activating element tabs may be automatically made available to activate the primary label composition at different ambient temperature reaction ranges and at different critical time-temperature integrals. Operator selection or weighing station intelligence would determine from perishable product identity the appropriate activator tab supply.

The visually-apparent endpoint of a critical time-temperature integral may take any convenient or intuitive form depending upon the anticipated arena within which its observance would be manifest. That is to say, the activator may be applied to the primary label composition in a distinct shape or design, such as would create or obscure a barcode to which in-market equipment would respond, or which would present a gradient-matching color density or colored warning message for the benefit of the purchasing consumer.

Direct thermal papers and other similar products comprising a primary high-temperature color-forming printing composition are widely known and commercially available from a number of industry sources. Each of this type of product, which finds ubiquitous use in facsimile machines, supermarket or food processor price/weight label machines, point-of-sale credit card registers, and the like, normally comprises a substrate coated with a mixture of co-reactant materials capable of forming a visually-distinct mark or color when exposed to elevated temperatures in excess of about 60° C. Commonly, these sheet products comprise a substrate of paper, polymer film, foil, or the like coated with a composition of co-reactant compounds or materials which combine at a predetermined temperature to form, in a normally irreversible reaction, a color highly contrasting with the unreacted composition background.

Thermally-responsive color-forming co-reactant compositions are well known in the art. Typical of such compositions are pH-sensitive combinations comprising azo dye precursors, co-reactant coupler compounds, and alkaline reaction initiators, or colorless or pale leuco dyes and proton-donating substances, i.e., acids, which together form a contrasting dye color upon application of prescribed temperature. The color-forming response of such compositions to applied heat may result directly from the inherent thermodynamics of the color-forming reaction, or may be due to activation of a thermolabile co-reactant or heat-initiated release of a co-reactant from protective encasement within a fusible matrix or encapsulation.

Representative of the myriad color-forming compositions and dye, acid co-reactant, and binder matrix components which are known in the art and which, although not per se constituting an essential part of the present invention, are particularly useful in its practice are color precursors such as fluoran, lactone, phthalide, or triaryl methane dyes, e.g., crystal violet lactone, 3, N-cyclohexyl-β-methyl-amino-6-methyl-7-anilino fluoran, or 3-pyrolidino-6-methyl-7-anilino fluoran, acid-producing co-reactants such as p-benzyl hydroxybenzoate, bisphenol A, phenolic condensation products, and low-melting organic acids or esters, and cellulosic and mono- and co-polymeric binder materials such as vinyl acetates, alcohols, or pyrrolidones and acrylates or acrylamides. Exhaustive lists of such known components and compositions may be found in the published art, for example, in patent literature by Iwata et al., U.S. Pat. No. 4,370,370; Glanz, U.S. Pat. No. 4,535,347; Arbree et al., U.S. Pat. No. 4,591,887; Kang, U.S. Pat. No. 4,898,849; Smith et al., U.S. Pat. No. 5,071,821; Kawakami et al., U.S. Pat. No. 5,288,688; and Hoffmann et al., U.S. Pat. No. 5,354,724; each of which is incorporated herein by reference.

BRIEF DESCRIPTION OF THE DRAWING

The present invention will be described with reference to the accompanying drawing of which.

DESCRIPTION OF THE INVENTION

Figure 1:
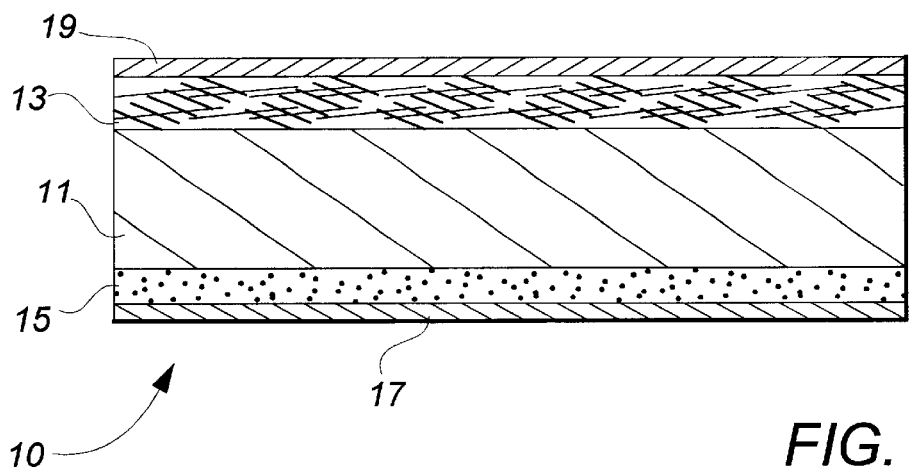
FIG. 1 depicts schematically in cross section an embodiment of a first element sheet product useful in the present invention comprising at least a first component of a primary thermographic color-forming composition.

As seen in FIG. 1, a preferred first element of the time-temperature indicator of the present invention is one selected from any number of widely-used, commercially-available direct thermal printing products, particularly such as self-adhesive label product 10 comprising a substrate 11 of paper, film, or the like bearing a heat-reactive color-forming layer 13. The underside of the substrate 11 is coated with a pressure-sensitive or low-temperature heat-activatable adhesive layer 15 which, when utilizing the former adhesive composition, bears a readily-detachable release sheet or film 17 that can be removed to allow adhesive attachment to a perishable product whose exposure to a time-temperature integral is to be monitored. As a precautionary measure for protecting reactive composition layer 13 from physical abuse or detrimental contaminants, such as oils or solvents, manufacturers often include an optional barrier layer 19.

In common usage, the upper surface of the label, as at layer 19, is selectively printed with heated indicia at a high temperature, e.g., in excess of about 60° C., as prescribed by the label stock manufacturer, to effect like selective reaction in composition layer 13 forming colored indicia indicating a product unit's weight, price, bar code identifier, and the like. The resulting printed label is then removed from a supply roll, usually automatically in the weighing device, for affixing by means of the adhesive layer to the product unit. The labeled product unit is then either returned to a safe storage environment, such as refrigeration for a foodstuff product, or is delivered to a waiting customer.

Figure 2:
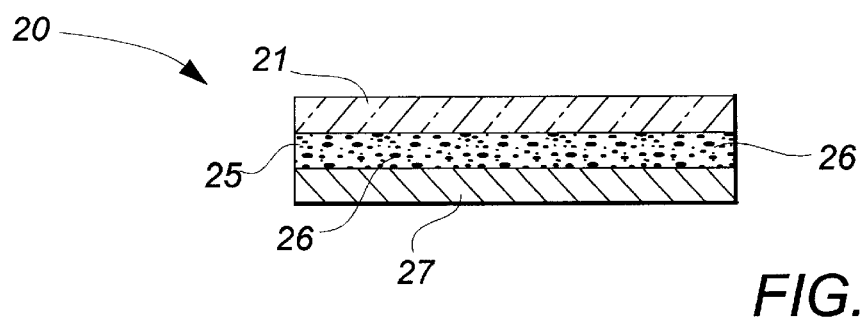
FIG. 2 depicts schematically in cross section an embodiment of a second element sheet product according to the present invention comprising a component for activating the thermographic color-forming composition of FIG. 1.

Such a direct thermal label product is incorporated into a time-temperature indicator system according to the present invention by applying on or, in the event of an incorporated protective layer 19, in close contact with thermally-responsive composition layer 13 a second activator element, such as shown at 20, in FIG. 2. A preferred embodiment of activator 20 takes the form of a small label or tab comprising a substrate 21 of a transparent film, e.g., of polyester, polycarbonate, polyolefin, or similar material commonly used in the coating arts, bearing a layer 25 of adhesive composition by which the tab is affixed to the outer surface of a direct thermal printed label 10, preferably during the label printing procedure outlined above. Where a pressure-sensitive adhesive is employed, activator element 20 will normally comprise a removable release-coated protective sheet 27.

According to the present invention, the composition of adhesive layer 25 comprises an activating component or composition 26 capable of initiating the direct thermal color-forming reaction upon contact with at least a first co-reactant component of the direct thermal composition 13. In a first embodiment, the activating component is itself a co-reactant which in combination with at least the first co-reactant component of the direct thermal composition will yield a color-forming composition which produces a visually-apparent color change, preferably at a rate approximating that of degradation of an associated perishable product, within a moderate ambient temperature range. For example, the activating component co-reactant may comprise an acid or a leuco dye which will form a reactive couple with the complementary component of the direct thermal composition.

Alternatively, in a second embodiment, the activating component or composition 26 will create an environment or condition under which the co-reactant components of the primary direct thermal reaction will react within the moderate ambient temperature range. In this embodiment, the activating component may solubilize at least one normally thermolabile co-reactant of the primary thermographic reaction, thereby enabling that reaction to proceed within the moderate temperature range. As a variant, the activating component may solubilize or otherwise act upon an intermediate component, such as an isolating matrix or encapsulating formation comprising layer 13, to cause release of the primary co-reactants and allow the reaction to proceed within the moderate temperature range.

Figure 3:
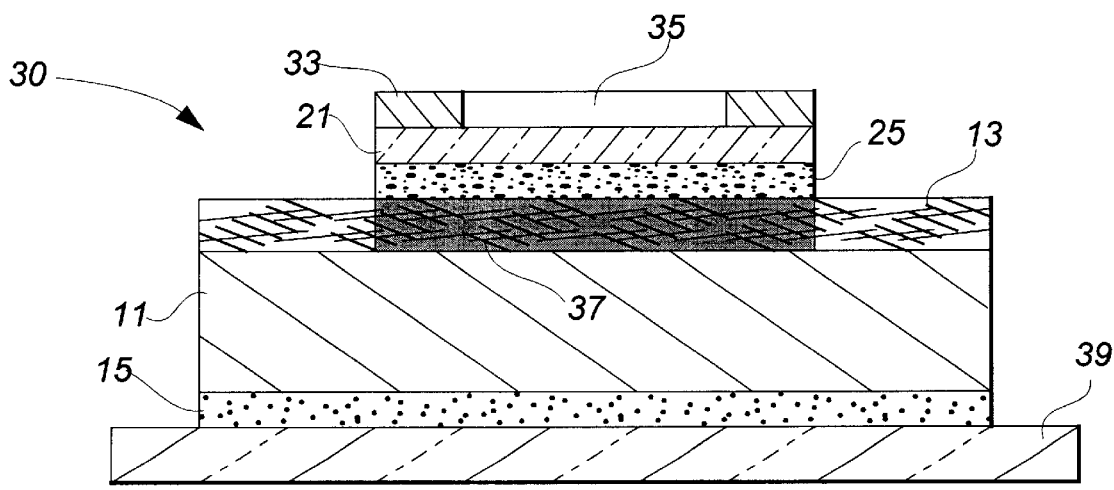
FIG. 3 depicts schematically in cross section the element sheets of FIGS. 1 and 2 assembled and attached to a wrapper of perishable product as in the practice of the present invention to yield an activated color-forming indicator system.

The effect of the activating element may be seen in the assemblage 30 shown in FIG. 3 where adhesive activating composition layer 25 of an activating tab is affixed in direct contact with primary direct thermal composition layer 13. Embodiment variants may also be seen in which the direct thermal label product is of an alternative type devoid of an optional protective top layer 19, and the activating tab includes a further member layer 33 in the form of an overprinted mask having an open central area 35 through which the underlying color composition layer 13 may be seen. This mask may be used to provide a reference for monitoring the progress of color formation, as will be described in more detail below. As also shown, the activated label combination is affixed by label adhesive layer 15 to the surface of packaging material 39 enclosing a unit of perishable product to be monitored.

Upon application of the activating tab to the product label, the activating component of composition 25 combines with one or more of the contiguous components of layer 13 to yield an activated region 37 of the primary thermographic composition. That region is thereby enabled to proceed with the prescribed color-forming reaction within a moderate temperature range that is considerably below the threshold of about 60° C. for direct thermal printing of the label, and is reasonably equivalent to an ambient within which there readily occurs deterioration of a perishable product in question. It is in this manner that the activated label is able to satisfy the purpose of the present time-temperature indicator system to respond to ambient temperature variations beyond the range of those conducive to safe storage of the perishable product and to ultimately signal, by exhibiting a predetermined level of developed color density, that a safe time-temperature integral has been exceeded and that, therefore, the safety or useful quality of the associated unit of perishable product should be questioned.

Figure 4:
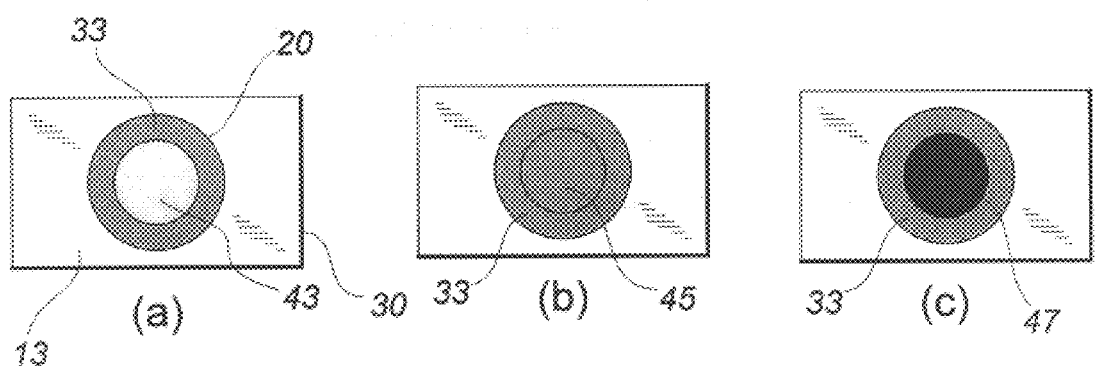
FIG. 4 depicts schematically in plan views (a)–(c) the progressive deepening of color with time-temperature integral in an activated system combination shown in FIG. 3.

Response of an activated label system of FIG. 3 may be seen in FIG. 4 where, at stage (a) existing at the time of activation, combination 30 comprises a disc-like activating tab 20 which includes mask 33 printed in ordinary ink at a color density selected to match the anticipated density of the color which will form during the predetermined critical time-temperature integral. At this stage the normal low-density color of the unreacted direct thermal color-forming composition may be viewed through the mask window at 43. With the passage of sufficient time during which the perishable product is exposed to varying temperatures cumulatively satisfying the critical time-temperature integral of the activated label, the color density of the viewable reacted label composition 45, as at stage (b), reaches that of mask 33, signaling the end of useful product shelflife. Further exposure of the product to additional time-temperature integral results in a window signal density 47, as at stage (c), well in excess of threshold 33, alerting a user to the potential of seriously degraded product quality.

Figure 5:
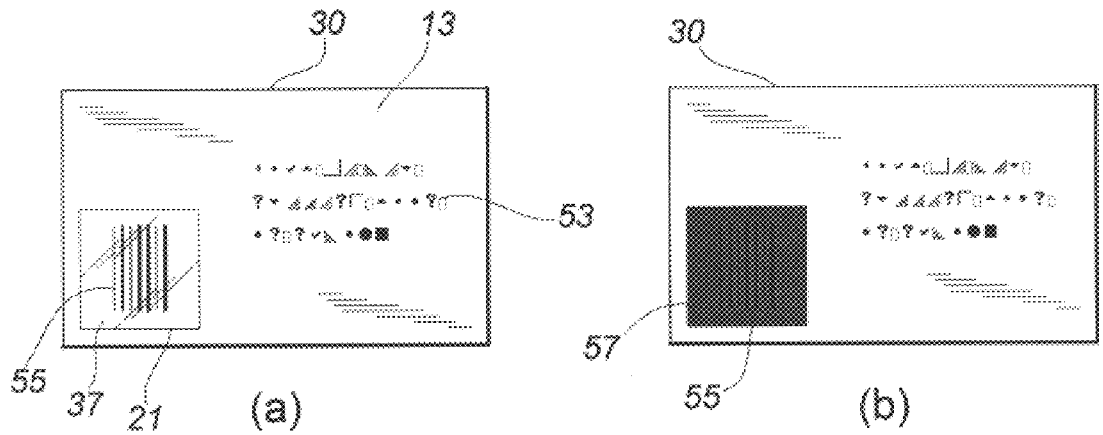
FIG. 5 depicts schematically in plan views (a)–(b) the progressive formation of color formation with time-temperature integral in an activated region of a thermally-printed product label which ultimately obscures a bar code signaling the expiration of product shelflife.

A variant utilization of the present time-temperature indicator system may be seen in FIG. 5 where, at activation stage (a), the direct thermal composition layer 13 of composite label 30 has been thermally printed with indicia 53 indicating weight, price, and the like, including a product-identifying barcode 55. An activating tab comprising transparent sheet 21 has been affixed to label composition layer 13 in such a position that the activated region 37 of layer 13 composition is coextensive with barcode 55. Upon expiration, at stage (b), of useful shelflife of the associated perishable product, i.e., upon accumulation of the critical time-temperature integral, the color density of the reacting color-forming composition region 57 has reached a level which obscures or alters barcode 55 sufficiently to register in market computer systems as a failed or unsafe product.

Figure 6:
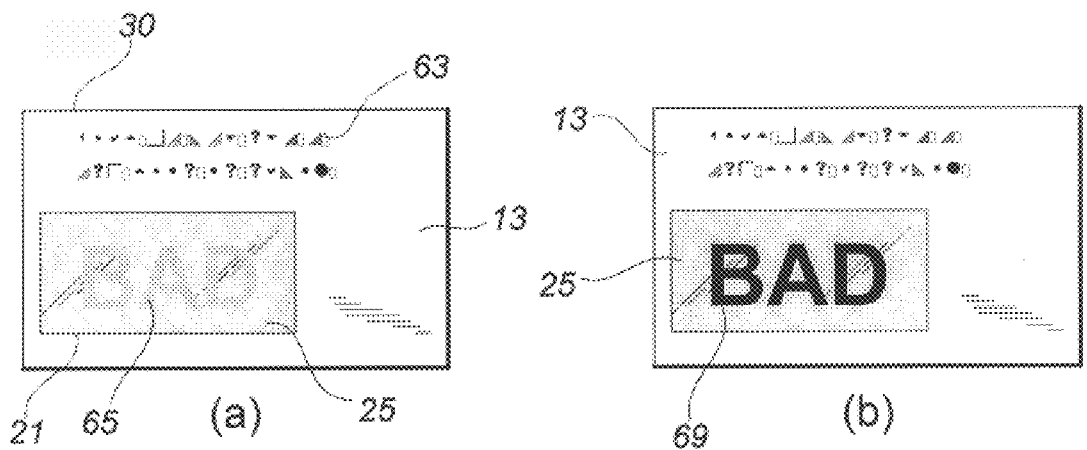
FIG. 6 depicts schematically in plan views (a)–(b) the progressive formation of color in the selectively-activated region of a thermally-printed product label which ultimately darkens with time-temperature integral to present a message signaling the expiration of product shelflife.

FIG. 6 depicts a similar utilization of the present indicator which addresses the needs of a customer. Thus, at activation stage (a), label system 30 printed with usual product-related direct thermal indicia 63 has affixed to color composition layer 13 an activating tab whose transparent support film 21 bears adhesive composition layer 25 in which the low-color-density activator component is situated, as by printing during the manufacture of the tab, in the form of recognizable indicia or message 65. After the critical time-temperature integral has transpired, as at stage (b), the activated region of direct thermal composition layer 13 has acquired a reacted higher color density 69 which is sufficient contrasting with background adhesive composition 25 to warn the consumer of a dangerous product condition.

From the foregoing description, it will be apparent to those skilled in the art that the predetermination of the critical time-temperature integral for a particular indicator system will depend upon two basic considerations. The first is the time factor, i.e., the rate of the color-forming reaction as determined by the participating co-reactants; the second being the temperature factor, i.e., the influence of the immediate ambient temperature upon such reaction rate. For example, a given leuco dye/acid co-reactant pair may proceed in the formation of a distinctly-colored dye at a nearly negligible rate at about 0° C., yet may achieve a vivid density over the course of a few hours at a moderately elevated temperature, e.g., room temperature of about 24° C., or instantaneously at direct thermal printing temperatures in excess of about 60° C. Thus, the rate of such color formation will vary with increments of ambient temperature throughout a predetermined operating range, thereby resulting in a preselected vivid end-point color density over a period of time determined by the intervening cumulative temperature effects, i.e., the "critical time-temperature integral".

In formulating an indicator system according to the present invention, therefore, one must take into account the parameters of operating temperature range and rate of color-forming development within such range. A major and novel advantage of the present invention in these considerations is that it provides means for establishing a known, finite initial time datum for operation of the indicator system, namely, the act of independent activation of the color-forming reaction and application of the newly-activated system to a perishable product under scrutiny at the instant the product is released from scrupulous control of acceptable ambient temperature. With this base datum established, the system composition formulator may concentrate on the selection of appropriate known co-reactant materials and compositions which will ensure a rate of color-development paralleling the rate of deterioration of a target perishable product.

Preparation of an indicator system comprising a dedicated color-forming composition, e.g., one in which the selection of both the primary and activating co-reactant components is entirely within the control of the system manufacturer, is a simple matter of empirical formulation, in the manner of the prior art, of a composition with a desired reaction rate. Such a rate may be determined by the color-forming reaction per se or by the inclusion of various types or concentrations of composition adjuncts, such as co-reactant solubilizers of varying melting point. Thus, a dedicated composition indicator system embodiment may comprise, in a first element layer 13 (FIG. 3), about 5 wt % crystal violet lactone dispersed in an acrylic binder matrix and, in a second activator element layer 25, about 4.5 wt % benzyl-4-hydroxybenzoate in a similar binder material with a sufficient amount of a phthalate plasticizer added to afford the resulting composition of layer 25 a self-adhesive tack for affixing to layer 13. The resulting activated region 37 of the composite indicator system will proceed to development of a desired end-point dye over a period of a few hours under an ambient of varying temperature. The level of reactivity of the color precursor/activator combination, and hence the critical time-temperature integral, may be varied as desired by variations in the co-reactant component concentrations or in coated layer thicknesses or visco-elastic properties. Any number of similar dedicated composition indicator system combinations may be readily derived from existing art by ordinary experimentation.

Yet another significant advantage of the present invention is the ability to economically incorporate existing staple direct thermal labeling products into an effective time-temperature indicator system. In this exceptional embodiment of the invention, one or more of the co-reactant components of the primary high-temperature direct thermal imaging, or color-forming, reaction composition of the label product is employed with the activating component of an applied activator tab element to lower the active temperature range of the primary imaging reaction, or to yield a secondary color-forming reaction which is active within a moderate ambient temperature range, to provide the desired visual change signaling expiration of a predetermined critical time-temperature integral. For example, the activating tab composition of layer 25 may simply comprise a solvent or high-boiling organic component, such as isophorone, hexylene glycol, or the like, to soften the matrix of label composition layer 13 and enable lower-temperature commingling of the co-reactant components in the primary composition. As a variant embodiment, the activator tab composition may comprise additional or different types of co-reactant to increase the rate of primary reaction in moderate ambients or constitute additional color-forming reactions to enhance the visual density of the indicator response.

Activator element compositions of embodiments of the present invention may further advantageously comprise activator components which enable utilization of the activator elements in conjunction with staple direct thermal label products comprising protective layer members 19 (FIG. 1). While such protective members comprise compositions formulated to mitigate the transient effect of extraneous oils, moisture, or solvent materials upon the primary direct thermal label components, activating compositions in layers 25 may readily be formulated to comprise solvents or penetrants which neutralize the effect of barrier or other protective means in order to enable activation of color-forming reactions. Such adjuncts may include persistent high-boiling solvent or humectant components which effectively overcome the temporary protection afforded by barrier layers and the like and enable the activation of underlying color-forming reactions. As extreme means for this purpose consideration might be given to physically abrasive or penetrating devices.

Although the foregoing outline of effective invention embodiments has, in the main, considered the novel activating element as comprising a composition layer coated on a supporting substrate, application of an activating component or co-reactant may be equally well effected in practice by fluid application or laminate transfer means. A clear ink comprising an activating co-reactant component may, for example, be applied in place of activating tab 21 (FIG. 5) to achieve the same result of obscuring barcode 55 at the expiration of the predetermined critical time-temperature integral.

In the light of the foregoing discussion of variant invention embodiments, the following examples will provide the skilled technician with further guidance toward effective formulation and fabrication of implementations of the present invention. In order to simplify evaluation of the described composition permutations and in view of the expected advantageous implementation of the invention in conjunction with commercially-available, staple direct thermal imaging products, these examples employ, for the most part, such representative direct thermal products as thermographic facsimile paper (AccuFax brand—PM Company, Cincinnati, Ohio) and direct thermal labels (Nashua brand—Nashua Corporation, Nashua, N.H.). The preparation and testing of samples in these examples employed common coating arts techniques, practices, and equipment, with indicated composition proportions being expressed, unless otherwise noted, on a weight basis.

EXAMPLE I

An activating tab product 20 (FIG. 2) comprising a first embodiment of the present invention comprises in the adhesive layer composition 25 an acid co-reactant 26 for the leuco dye comprising the typical direct thermal label product. The activator composition was prepared by mixing with a measure of a commercially-available organic-solvent-based multi-acrylic pressure-sensitive adhesive composition (Gelva 2497, Solutia, St. Louis, Mo.) a sufficient amount of a 30% solution of p-toluene-sulfonic acid monohydrate (PTSAM) in ethyl acetate to provide about 2.8% PTSAM in the resulting mixture. The mixture was then thinned with an organic coating vehicle solvent of moderate volatility (2-propanol) to provide a convenient coating viscosity and was applied to a 0.05 mm polyester film 21 using a common Meyer rod drawdown device to obtain a fluid coating of about 0.05–0.07 mm thickness which was air-dried at room temperature of about 24° C. to yield a tacky adhesive layer of about 0.04 mm. A sheet of common silicon-coated release paper 27 was applied to the adhesive layer to facilitate subsequent handling.

The prepared activator sheet material was cut into a number of conveniently-sized tabs 20 to be used in testing. Such a tab was adhesively affixed, after removal of cover sheet 27, to the reactive surface of a sheet of AccuFax thermographic fax paper to form a sample of activated time-temperature indicator system generally depicted at 30 in FIG. 3. The activated sample was maintained at constant temperature, or cycled through ambients of varying measured temperature, utilizing common laboratory oven or refrigeration equipment.

At selected times after activation, optical density of the color developing in the activated region underlying the sample tab was measured with an X-Rite 404 Portable Reflectance Densitometer operating in the cyan mode. Additional sample tabs varying in concentration of activating acid, PTSAM, in layer 25 were prepared and tested in like manner. Results of such testing at room temperature (RT) of about 24° C. are shown in Table I as optical density varying as a function of time after activation of the system. From such test variations an achieved optical density may be selected as the end-point indication of critical time-temperature integral for use with a prospective perishable product having a similar rate of degradation as that of the development of color in an activated label system.

TABLE I

Effect of Concentration of Activator Acid p-toluenesulfonic acid monohydrate (PTSAM) on the Developed Density of AccuFax Thermal Paper at RT (24° C.).

| Sample | PTSAM wt % | Optical Density (hours after activation) | | | | |
| --- | --- | --- | --- | --- | --- | --- |
| | | 0 | 0.5 | 1.1 | 2.2 | 3.1 |
| A | 0 | 0.14 | 0.14 | 0.14 | 0.14 | 0.14 |
| B | 2.8 | 0.14 | 0.38 | 0.52 | 0.66 | 0.72 |
| C | 5.8 | 0.17 | 0.49 | 0.70 | 0.78 | 0.80 |
| D | 7.5 | 0.15 | 0.69 | 0.87 | 0.90 | 0.90 |

EXAMPLE II

Figure 7:
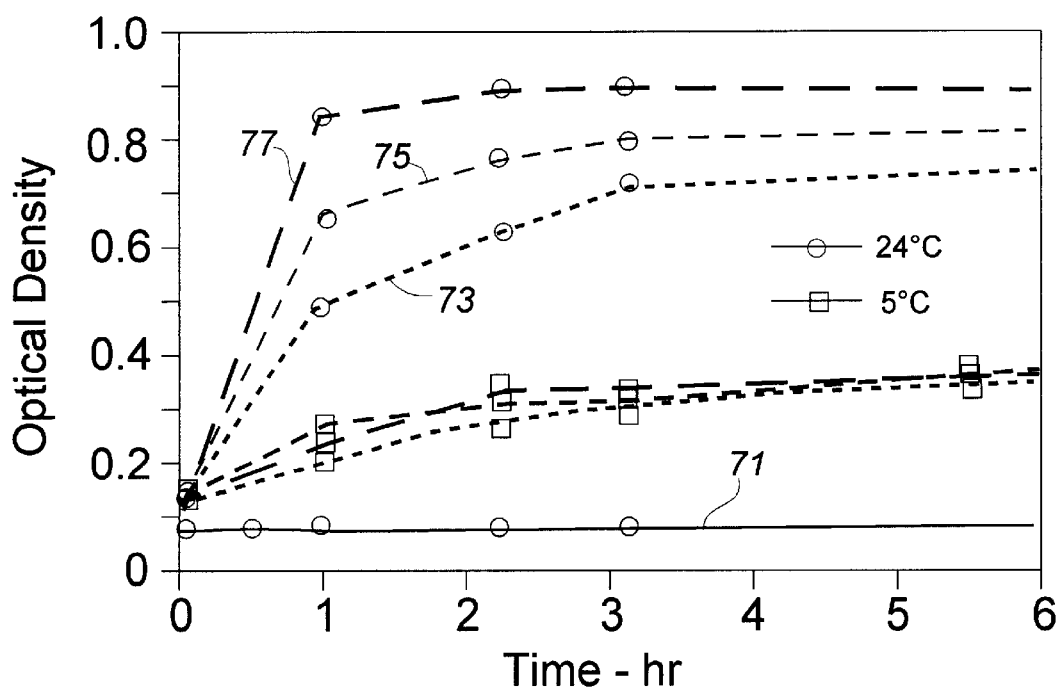
FIG. 7 is a chart plotting the effect of activator composition and temperature on the rate of color formation in embodiments of the invention.

Activated samples prepared as in Example I were tested for optical density variations during storage at room temperature and at 5° C. The results shown in Table II demonstrate the effect of varying temperature on the reaction rate of the activated indicator system. This effect is depicted graphically in FIG. 7 wherein there becomes more apparent the range of utility of an activator of the present invention in tracking exposure of perishable products to a dilatory time-temperature integral. In FIG. 7, the enumerated PTSAM concentrations of 0, 2.8, 5.8, and 7.5% are respectively represented in traces 71, 73, 75, 77.

TABLE II

Effect of Temperature on the Developed Density of AccuFax Thermal Paper Using Activator Acid p-toluenesulfonic acid monohydrate

| Sample | PTSAM wt % | Optical Density (hours after activation) | | | | |
| --- | --- | --- | --- | --- | --- | --- |
| | | 0 | 1.0 | 2.2 | 3.1 | 5.5 |
| A (24° C.) | 2.8 | 0.14 | 0.52 | 0.66 | 0.72 | 0.77 |
| A (5° C.) | 2.8 | 0.15 | 0.26 | 0.21 | 0.30 | 0.34 |
| B (24° C.) | 5.8 | 0.17 | 0.70 | 0.78 | 0.80 | 0.80 |
| B (5° C.) | 5.8 | 0.15 | 0.28 | 0.32 | 0.31 | 0.33 |
| C (24° C.) | 7.5 | 0.15 | 0.87 | 0.90 | 0.90 | 0.90 |
| C (5° C.) | 7.5 | 0.16 | 0.27 | 0.33 | 0.32 | 0.35 |

EXAMPLE III

Test samples prepared in the manner of Example I were used to activate another type of direct thermal product, namely, Nashua NT7433. As seen from the results shown in Table III this label stock is less reactive to a given activator agent, for the most part due to the presence of a barrier coating.

TABLE III

Effect of Concentration of Activator Acid p-toluenesulfonic acid monohydrate on the Developed Density of Nashua NT7433 Direct Thermal Paper at RT (24° C.).

| Sample | PTSAM wt % | Optical Density (hours after activation) | | | | |
| --- | --- | --- | --- | --- | --- | --- |
| | | 0 | 1.0 | 2.0 | 3.5 | 5.0 |
| A | 2.8 | 0.15 | 0.16 | 0.16 | 0.16 | 0.16 |
| B | 5.8 | 0.16 | 0.16 | 0.22 | 0.29 | 0.29 |
| C | 7.5 | 0.17 | 0.23 | 0.35 | 0.55 | 0.66 |

EXAMPLE IV

Figure 8:
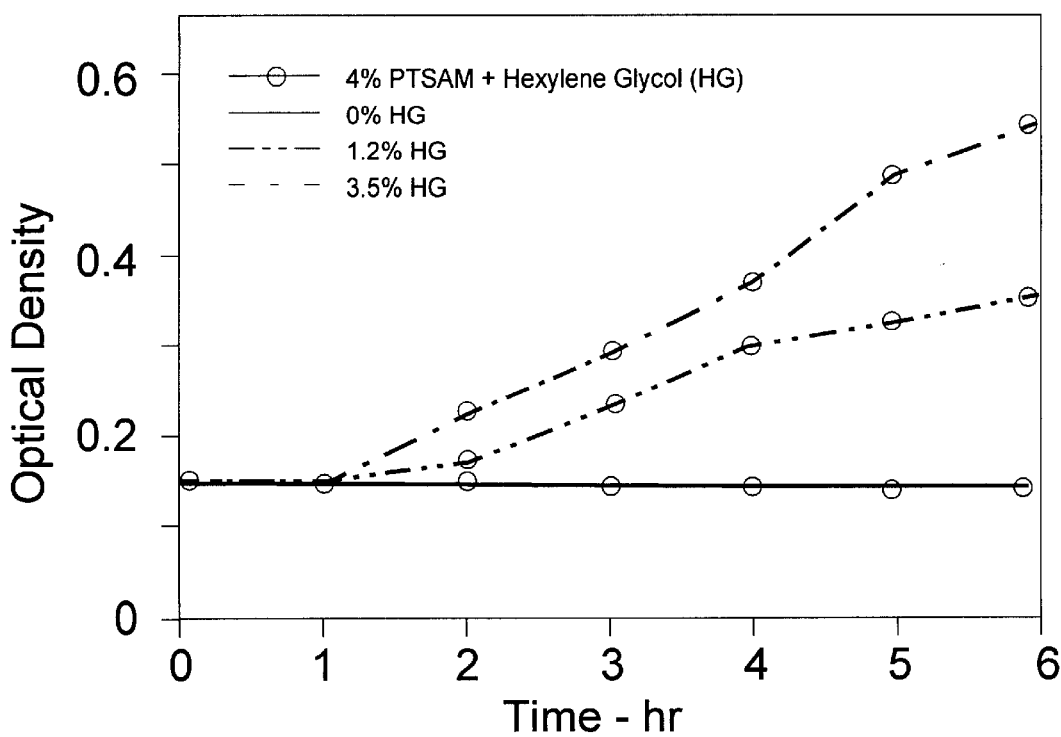
FIG. 8 is a chart plotting the effect of enhanced activator composition on the rate of color formation in embodiments of the invention.

Activator tabs were prepared as in Example III employing activator compositions comprising 4% PTSAM and varying amounts of an additional humectant component, hexylene glycol (HG). The resulting tabs were used to activate Nashua NT7433 direct thermal label paper with the results shown in Table IV. The effect of improved barrier layer penetration and fluid reaction medium provided by this added component are apparent in these results and as graphically depicted in FIG. 8.

TABLE IV

Effect of Added Hexylene Glycol in Gelva/4% PTSAM on the Developed Density of Nashua NT7433 Thermal Paper at RT (24° C.).

| Sample | Hexylene Glycol wt % | Optical Density (hours after activation) | | | | | | |
| --- | --- | --- | --- | --- | --- | --- | --- | --- |
| | | 0 | 1 | 2 | 3 | 4 | 5 | 6 |
| I | 0 | 0.16 | 0.16 | 0.17 | 0.16 | 0.16 | 0.17 | 0.16 |
| J | 1.2 | 0.15 | 0.15 | 0.17 | 0.24 | 0.30 | 0.32 | 0.36 |
| K | 3.5 | 0.15 | 0.15 | 0.22 | 0.29 | 0.37 | 0.48 | 0.55 |

EXAMPLE V

Activator tab samples prepared in the manner of Example IV and comprising 4% PTSAM and 7.7% HG were used to activate AccuFax paper. The rates of response of the resulting activated indicator system at refrigeration (4° C.) and room (24° C.) temperatures which could similarly affect the rate of foodstuff deterioration are shown in Table V.

TABLE V

Effect of Temperature for 7.7% HG/4% PTSAM on the Rate of Developed Color Density of AccuFax Paper.

| | Optical Density (hours after activation) | | | | | | |
|---|---|---|---|---|---|---|---|
| Sample | 0 | 1 | 2 | 3 | 4 | 5 | 6 |
| L (24° C.) | 0.19 | 0.68 | 0.83 | 0.94 | 1.00 | 1.08 | 1.23 |
| M (4° C.) | 0.15 | 0.25 | 0.26 | 0.26 | 0.26 | 0.28 | 0.28 |

EXAMPLE VI

Activator tabs were prepared in the manner of Example I with the exception of the use of a weaker acid activator component, Bisphenol A, in place of PTSAM. Results of the effects of these tabs on AccuFax paper as an indicator system at (50° C.) are shown in Table VI.

TABLE VI

Effect of Concentration of Activator Acid Bisphenol A on the Developed Density of AccuFax Thermal Paper at 50° C.

| | Bisphenol A | Optical Density (hours after activation) | |
|---|---|---|---|
| Sample | wt % | 0 | 1.0 |
| N | 0 | 0.13 | 0.16 |
| O | 4.0 | 0.13 | 0.32 |
| P | 10.0 | 0.15 | 0.40 |

EXAMPLE VII

Activator tab samples were prepared as in Example VI with the addition of about 10% of a high-boiling organic solvent, isophorone (BP 214° C.) and were applied to activate AccuFax paper. This additional solvent component, which remains part of the activating composition, increases the fluidity of the color-forming reaction medium and results in a higher indicator system response rate as seen in Table VII.

TABLE VII

Effect of Concentration of Activator Acid Bisphenol A with 10% Isophorone on the Developed Density of AccuFax Thermal Paper at 50° C.

| | Bisphenol A | Optical Density (hours after activation) | |
|---|---|---|---|
| Sample | wt % | 0 | 1.0 |
| Q | 0 | 0.13 | 0.16 |
| R | 2.0 | 0.13 | 0.34 |
| S | 4.0 | 0.27 | 0.43 |
| T | 7.0 | 0.24 | 0.67 |
| U | 10.0 | 0.25 | 0.83 |

EXAMPLE VIII

A number of activator tab samples were prepared in the manner of Example I utilizing as an activator acid the ester, benzyl-4-hydroxybenzoate (B4HB). This component was incorporated at the rate of about 5% into the Gelva 2497 adhesive matrix of a number of different activator compositions as a 35% solution in different vehicle solvents. Since little of these solvents remains in the final activator composition, the response rates of activated indicator systems with AccuFax paper at 50° C., as shown in Table VIII, are quite similar.

TABLE VIII

Effect of Activator Acid Benzyl-4-hydroxybenzoate from Various Solvents on the Developed Density of AccuFax Thermal Paper at 50° C.

| | | | Optical Density (hours after activation) | |
|---|---|---|---|---|
| Sample | B4HB wt % | Solvent | 0 | 1.0 |
| 1 | 0 | Ethyl Acetate | 0.13 | 0.14 |
| 2 | 4.9 | Methanol | 0.13 | 0.41 |
| 3 | 4.8 | 2-propanol | 0.14 | 0.41 |
| 4 | 5.2 | Ethyl Acetate | 0.14 | 0.43 |
| 5 | 5.1 | Isophorone | 0.13 | 0.45 |
| 6 | 5.0 | Ethyl Lactate | 0.14 | 0.40 |
| 7 | 5.7 | Pgeea* | 0.14 | 0.45 |
| 8 | 5.2 | Ethanol | 0.14 | 0.43 |
| 9 | 4.9 | 1-amylmethyl ketone | 0.14 | 0.43 |

*Propylene glycol ethyl ether acetate

EXAMPLE IX

Activator tabs were prepared in the manner of Example VIII employing varying concentrations of B4HB in methanol vehicle solvent. Effect of change of activator concentration on the developed density of AccuFax Thermal Paper at 24° C. is shown in Table IX. A similar effect was obtained with Nashua NT7433 Direct Thermal paper.

TABLE IX

Effect of Concentration of Activator Acid Benzyl-4-hydroxybenzene (B4HB) on the Developed Density of AccuFax Thermal Paper at RT (24° C.).

| | B4HB | Optical Density (hours after activation) | | | | | |
|---|---|---|---|---|---|---|---|
| Sample | wt % | 0 | 1 | 2 | 4 | 19 | 27 |
| 10 | 0 | 0.13 | 0.13 | 0.13 | 0.13 | 0.13 | 0.13 |
| 11 | 5 | 0.14 | 0.15 | 0.17 | 0.17 | 0.22 | 0.23 |
| 12 | 10 | 0.14 | 0.18 | 0.23 | 0.26 | 0.35 | 0.36 |
| 13 | 15 | 0.14 | 0.25 | 0.32 | 0.38 | 0.52 | 0.54 |

EXAMPLE X

Activator tabs of enhanced stability were prepared in the manner of Example I employing as activator component the photoacid compound, 2-nitrobenzaldehyde. This component provides the additional advantage of further ensuring a finite activation time datum beyond that generally established by application of an activating tab to a co-reactant label. This embodiment ameliorates any errant activation conditions by requiring exposure of the tab composition to actinic radiation, such as intense ultraviolet light, in order to generate the acid component and effect activation of the system. The effect of various vehicle solvents on the photoacid incorporation was examined in the manner of Example VIII, with the results shown in Table X. Similarly reinforcing activation requirements are achieved with microencapsulated activating high-boiling solvent dispersed within the activator tab matrix. In such an embodiment, the subjective application of pressure to an affixed activating tab is required to activate the indicator system.

TABLE X

Effect of UV Light-Activated Photoacid 2-Nitrobenzaldehyde (2NB) on the Developed Density of AccuFax Thermal Paper at RT (24° C.).

| | 2NB | | Optical Density (hours after activation) | | | |
|---|---|---|---|---|---|---|
| Sample | wt % | Solvent | 0 | 1.0 | 1.5 | 1.7 |
| 14 | 0 | Ethyl Acetate | 0.13 | 0.13 | 0.13 | 0.13 |
| 15 | 4.9 | Methanol | 0.13 | 0.16 | 0.23 | 0.30 |
| 16 | 4.8 | 2-propanol | 0.14 | 0.17 | 0.24 | 0.36 |
| 17 | 5.2 | Ethyl Acetate | 0.13 | 0.15 | 0.20 | 0.31 |
| 18 | 5.1 | Isophorone | 0.14 | 0.16 | 0.22 | 0.32 |
| 19 | 5.0 | Ethyl Lactate | 0.13 | 0.15 | 0.22 | 0.29 |
| 20 | 5.7 | Pgeea* | 0.13 | 0.16 | 0.23 | 0.30 |
| 21 | 5.1 | Hexylene Glycol | 0.14 | 0.16 | 0.25 | 0.34 |
| 22 | 5.0 | Propylene Glycol | 0.13 | 0.15 | 0.19 | 0.32 |
| 23 | 5.7 | Toluene | 0.14 | 0.16 | 0.23 | 0.29 |
| 24 | 5.2 | Ethanol | 0.13 | 0.16 | 0.22 | 0.31 |
| 25 | 4.9 | 1-amylmethyl ketone | 0.13 | 0.16 | 0.27 | 0.29 |

*Propylene glycol ethyl ether acetate

EXAMPLE XI

Activator tabs were prepared in the manner of Example I employing instead of the organic-solvent-based Gelva adhesive composition a commercially-available aqueous-dispersion-based multi-acrylic pressure-sensitive adhesive composition, Kiwo D185 KIWO, Seabrook, Tex.). In addition, the PTSAM activator acid was with trichloroacetic acid (TCA). The efficacy at 24° C. of such activator tabs applied to AccuFax Thermal Paper appears in Table XI.

TABLE XI

Effect of Concentration of Activator Acid Trichloroacetic acid (TCA) in Kiwo D158 Adhesive on the Developed Density of AccuFax Thermal Paper at RT (24° C.).

| | TCA | Optical Density (hours after activation) | | |
|---|---|---|---|---|
| Sample | wt % | 0 | 1.0 | 3.0 |
| 26 | 0 | 0.12 | 0.12 | 0.12 |
| 27 | 3.0 | 0.13 | 0.31 | 0.41 |
| 28 | 5.1 | 0.15 | 0.53 | 0.75 |
| 29 | 8.7 | 0.16 | 0.88 | 1.21 |
| 30 | 9.9 | 0.18 | 0.88 | 1.24 |

EXAMPLE XII

Activator tabs prepared in the manner of Example XI were employed with a dedicated co-reactant color-forming composition comprising a commercially-available irreversible thermochromic ink (CTI Dynacolor, Chromatic Technologies). The primary color-forming system component sheet was prepared by coating a layer of the ink by means of a coating rod device on common printing paper stock and drying at room temperature. Activator tabs comprising about 5% TCA were applied to the resultant co-reactant sheet and the rate of color density development of the activated system at 24° C. was measured as shown in Table XII.

TABLE XII

Effect of TCA in Kiwo D158 Adhesive on the Developed Density of CTI Dynacolor Thermochromic Ink at RT (24° C.).

| | TCA | Optical Density (hours after activation) | | | | | |
|---|---|---|---|---|---|---|---|
| Sample | wt % | 0 | 0.3 | 0.6 | 1.3 | 1.5 | 19.0 |
| 31 | 0 | 0.42 | — | — | — | — | 0.40 |
| 32 | 5.1 | 0.50 | 0.66 | 0.85 | 0.95 | 1.20 | 1.62 |

EXAMPLE XIII

Activator tabs were prepared in the manner of Example I utilizing 4.2% trichloroacetic acid (TCA) instead of PTSAM. Tab samples were also prepared in which the activator composition comprising 4.2% TCA in the Gelva 2497 matrix included an additional 2.5% decanol (DOH–MP 6.4° C.). The activator tabs were affixed to sheets of the dedicated co-reactant CTI Dynacolor ink composition and the optical densities of the resulting activated system samples were measured immediately and after about 16 hr refrigeration at 2° C. at which time neither sample exhibited significant increase in color density. The samples were then removed to a room temperature ambient of about 24° C. and the progression of color-forming density was measured over the course of a few hours. The effect of the DOH fluidizing agent in accelerating the color formation is evident in the results shown in Table XIII.

TABLE XIII

Effect of 2.5% decyl alcohol (DOH) with TCA in Gelva 2497 Adhesive on the Developed Density of CTI Dynacolor Thermochromic Ink at RT (24° C.).

| | DOH | Optical Density (hours after activation) | | | | |
|---|---|---|---|---|---|---|
| Sample | wt % | 0 | 1.0 | 2.0 | 3.8 | 5.0 |
| 33 | 0 | 0.47 | 0.62 | 0.73 | 0.90 | 1.00 |
| 34 | 2.5 | 0.47 | 0.76 | 0.95 | 1.17 | 1.25 |

In a variation of this example, activator tabs were prepared comprising n-decanoic acid (NDA–MP 31° C.) and were applied to AccuFax Thermal Paper. During storage at room temperature (24° C.) the activator composition was isolated from contact with the color-forming paper composition due to its stable crystalline nature and the paper exhibited little color density development over a period of a few hours. The activated sample was then removed to an ambient of about 37° C. in which it developed within a few minutes an outstanding color density substantially equal to that achieved in the AccuFax paper at its prescribed printing temperature of about 60° C. Such an activator variant thus provides a dual function of initiating a pre-selected mid-temperature range time-temperature integral reaction while also being capable of signaling even a momentary excursion beyond, and in the same context certifying non-exposure to, a pre-designated threshold temperature limit which could be immediately destructive of the monitored product's viability, as with certain antibiotics or vaccines.

EXAMPLE XIV

A number of direct thermal label papers comprise a barrier coating over the color precursor composition layer for the purpose of preventing physical damage or penetration of contaminating oils, solvents, or the like. The effect of such barrier coatings must be taken into account if it is intended to employ commercially-available direct thermal labels as components of the activatable time-temperature indicator systems of the present invention. The results of utilizing an activator tab comprising a combination of hexylene glycol humectant with a Gelva 2497 adhesive composition comprising 5% activator acid co-reactant component, in connection with barrier-layer (Nashua NT5726) and barrier-free (Nashua NT8821) direct thermal papers is shown in Table XIV.

TABLE XIV

Comparison of Developed Density of Barrier-Layer And Barrier-Free Direct Thermal Paper in Response to Gelva 2497/5% TCA/Hexylene Glycol Activator Composition at RT (24° C.).

| Sample | Barrier Layer | Hexylene Glycol wt % | Optical Density (hours after activation) | | | |
|---|---|---|---|---|---|---|
| | | | 0 | 1.0 | 2.2 | 4.0 |
| 35 | Yes | 0 | 0.15 | 0.14 | 0.15 | 0.14 |
| | No | 0 | 0.13 | 0.32 | 0.45 | 0.52 |
| 36 | Yes | 4.6 | 0.14 | 0.15 | 0.14 | 0.14 |
| | No | 4.6 | 0.14 | 0.56 | 0.78 | 0.94 |
| 37 | Yes | 9.0 | 0.13 | 0.14 | 0.14 | 0.13 |
| | No | 9.0 | 0.13 | 1.10 | 1.45 | 1.67 |
| 38 | Yes | 12.8 | 0.14 | 0.14 | 0.14 | 0.13 |
| | No | 12.8 | 0.19 | 2.10 | 2.25 | 2.25 |
| 39 | Yes | 17.3 | 0.14 | 0.14 | 0.14 | 0.14 |
| | No | 17.3 | 0.20 | 2.17 | 2.23 | 2.25 |

It is anticipated that other embodiments and variation of the present invention will become readily apparent to the skilled artisan in the light of the foregoing description and examples, and such embodiments and variations are intended to likewise be included within the scope of the invention as set out in the appended claims.

What is claimed is:

1. An activatable time-temperature monitoring system for indicating the elapse of a combination of time and ambient temperature which exceeds a predetermined time-temperature integral
   characterized in that said system comprises
   a) a first element comprising a direct thermal color-forming composition comprising at least a pair of co-reactant components capable of reacting in combination to form said color upon the heating of said composition at least to a threshold temperature; and
   b) a second element comprising an activating component capable of, upon contact with said first element composition, initiating said color-forming combination reaction at a second temperature below said threshold and causing said reaction to proceed at an average rate satisfying said predetermined time-temperature integral.

2. A system according to claim 1
   characterized in that
   a) said first element co-reactant components of said composition are normally maintained in non-reactive separation; and
   b) said activating component is capable of effecting reactive contact between said co-reactant components at least at said second temperature.

3. A system according to claim 2
   characterized in that
   a) said non-reactive separation of said components is effected by an intervening matrix material, and
   b) said activating component is capable of effecting a condition in said matrix enabling said reactive component contact.

4. A system according to claim 3 wherein said activating component increases a fluid property of said matrix to enable migrative contact between said co-reactant components.

5. A system according to claim 1 wherein said activating component exhibits at said second temperature a reactant property of at least one of said pair of co-reactant components.

6. A system according to claim 1
   characterized in that
   a) said first element comprises a pH-sensitive dye-forming composition; and
   b) said activating component is capable of providing at least at said second temperature a condition of pH conducive to the formation of said dye.

7. An activatable time-temperature monitoring system for indicating the accumulation of a combination of time and ambient temperature which exceeds a predetermined time-temperature integral to which an associated perishable product has been exposed
   characterized in that said system comprises
   a) a first element comprising a direct thermal color-forming composition comprising at least a pair of co-reactant components capable of reacting in combination to form said color upon the heating of said composition at least to a threshold temperature; and
   b) a second element comprising an activating component capable of, upon contact with said first element composition, initiating said color-forming combination reaction at a second temperature below said threshold and causing said reaction to proceed to formation of said color at an average rate satisfying said predetermined time-temperature integral.

8. A system according to claim 7 wherein said activating component exhibits at least at said second temperature a reactant property of at least one of said pair of co-reactant components.

9. A system according to claim 8 wherein
   a) said activating component is normally maintained out of contact with said first element composition; and
   b) said second element further comprises a component capable of effecting said reaction-initiating contact at least at said second temperature.

10. A system according to claim 7 wherein
    a) said first element co-reactant components are normally maintained out of reactive combination; and
    b) said activating component comprises a composition capable of effecting said reactive combination of said co-reactant components.

11. A system according to claim 10 wherein said activating component is capable of effecting a salvation of said direct thermal composition.

12. A system according to claim 7 wherein
    a) at least one of said direct thermal composition component pair is reactive in an acid medium to form said color; and
    b) said activating component comprises a source of acid capable of generating said acid medium at least at said second temperature.

13. A system according to claim 12 wherein said activating component further comprises a composition capable of increasing the fluidity of said direct thermal composition.

14. A system according to claim 7 wherein
   a) said combination reaction proceeds in response to said activating component at a rate varying within a given range, and
   b) said second element further comprises a second activating component capable of so activating said combination reaction at least at a third temperature intermediate said second and threshold temperatures and causing said reaction to proceed at a rate substantially above said given range.

15. A system according to claim 7 wherein said activating component is selectively disposed on said second element in the form of intelligible indicia, thereby providing for a visually-distinct reproduction of said indicia as a result of said initiated color-forming reaction.

16. A system according to claim 7 wherein said activating component is selectively disposed in a position relative to indicia on said first element so as to cause the obscuring or alteration of said indicia as a result of said initiated color-forming reaction.

17. A method of monitoring the useful life of a perishable product which comprises affixing to said product a time-temperature monitoring system for indicating by means of a visually distinct color change signal the accumulation of a combination of time and ambient temperature which exceeds a predetermined time-temperature integral to which an associated, perishable product has been exposed characterized in that
   a) said indicator system comprises
      1) a first element comprising a direct thermal color-forming composition comprising at least a pair of co-reactant components capable of reacting in combination to form said color upon the heating of said composition at least to a threshold temperature, and
      2) a second element comprising an activating component capable of, upon contact with said first element composition, initiating said color-forming combination reaction at a second temperature below said threshold and causing said reaction to proceed to the formation of said color at an average rate satisfying said predetermined time-temperature integral;
   b) said second element is affixed to said first element to thereby effect said contact between said activator component and said first element color-forming composition;
   c) said first element is affixed to said perishable product substantially simultaneously with said affixing of said second element to said first element; and
   d) said perishable product is exposed to ambient temperatures for a time within the period up to the formation of said color and the resulting appearance of said visually distinct signal.

18. A method according to claim 17 wherein
   a) the activity of said activator component is rendered latent by protective encapsulation; and
   b) said method further comprises rupturing said encapsulation to thereby initiate said activity of said activator component.

19. A method according to claim 17 wherein
   a) said activator component comprises a latent actinically-activatable compound; and
   b) said method further comprises exposing said compound to actinic radiation to thereby initiate said activity of said activator component.

20. A method according to claim 17 wherein
   a) a series of second elements is provided varying in level of time-temperature integral of resulting activated reaction, and
   b) a second element to be affixed to said first element is selected from said series according to a designation of a type of perishable product to which said first element is to be affixed.

* * * * *